(12) United States Patent
Gentle et al.

(10) Patent No.: US 9,095,731 B2
(45) Date of Patent: Aug. 4, 2015

(54) ANTI-MICROBIAL COMPOSITION

(75) Inventors: Thomas M. Gentle, St. Michael, MN (US); Adam W. Hauser, Minneapolis, MN (US); Lisa A. Colomina, Waconia, MN (US)

(73) Assignee: Medivators Inc., Minneapolis, MN (US)

( * ) Notice: Subject to any disclaimer, the term of this patent is extended or adjusted under 35 U.S.C. 154(b) by 0 days.

(21) Appl. No.: 13/303,315

(22) Filed: Nov. 23, 2011

(65) Prior Publication Data

US 2012/0134953 A1    May 31, 2012

Related U.S. Application Data

(60) Provisional application No. 61/416,653, filed on Nov. 23, 2010.

(51) Int. Cl.

| | |
|---|---|
| *A01N 55/10* | (2006.01) |
| *A61Q 17/00* | (2006.01) |
| *A61K 8/34* | (2006.01) |
| *A61K 8/81* | (2006.01) |
| *A61K 8/898* | (2006.01) |
| *A01N 33/12* | (2006.01) |
| *A01N 55/00* | (2006.01) |

(52) U.S. Cl.
CPC .............. *A61Q 17/005* (2013.01); *A01N 33/12* (2013.01); *A01N 55/00* (2013.01); *A61K 8/34* (2013.01); *A61K 8/8129* (2013.01); *A61K 8/898* (2013.01)

(58) Field of Classification Search
CPC ......... A61K 8/86; A61K 8/34; A61K 8/8129; A61Q 17/005
USPC .............................................. 424/78; 514/23
See application file for complete search history.

(56) References Cited

U.S. PATENT DOCUMENTS

| | | | |
|---|---|---|---|
| 4,721,511 A | 1/1988 | Kupits | |
| 6,572,926 B1 | 6/2003 | Morgan et al. | |
| 7,637,271 B1 * | 12/2009 | Cumberland et al. | ....... 134/25.2 |
| 2006/0217515 A1 | 9/2006 | Getman et al. | |
| 2006/0223962 A1 * | 10/2006 | Getman et al. | .................. 528/10 |
| 2010/0322890 A1 | 12/2010 | Edwards | |

FOREIGN PATENT DOCUMENTS

WO    WO2011005951 A2    1/2011

OTHER PUBLICATIONS

Richards R M; Microbios, 1981, 31(124):83-91) published by UK Pubmed central.*
Product information (MSDS) of lemon oil, published by Florida Chemical, Inc. Oct. 2006.*
Product information of lemon oil, published by CAMEO Chemicals, 1992.*
Gol'dberg, M; Title: Entsiklopediia polimerov, vol. 2. Moscow, 1974. An English translation is referenced. See PDF downloaded from http://encyclopedia2.thefreedictionary.com /Film-Forming+Material.*
Davis et al., Title: Household Cleaners: Environmental evaluation and proposed standards for general purpose household cleaners, Jul. 1992.*
International Search Report and Written Opinion issued in PCT/US2011/062008, mailed Apr. 10, 2012, 10 pages.

* cited by examiner

*Primary Examiner* — Ali Soroush
*Assistant Examiner* — Yanzhi Zhang
(74) *Attorney, Agent, or Firm* — Faegre Baker Daniels LLP

(57) ABSTRACT

Anti-microbial compositions including an anti-microbial polymer containing silicon-containing quaternary ammonium groups, polyvinyl alcohol (PVA), at least one short chain alcohol, optional fragrance, and water are provided. The anti-microbial compositions may be used to disinfect both porous and non-porous surfaces. Exemplary compositions may include 0.1-10 wt % of the anti-microbial polymer containing silicon-containing quaternary ammonium groups, 0.1-10 wt % polyvinyl alcohol (PVA), 1.0-20 wt % isopropyl alcohol, optional fragrance, and water.

9 Claims, No Drawings

ANTI-MICROBIAL COMPOSITION

CROSS-REFERENCE TO RELATED APPLICATION

This application claims the benefit under 35 U.S.C. Section 119(e) of U.S. Provisional application 61/416,653 entitled "Anti-Microbial Surface Treatment," which is hereby incorporated by reference in its entirety.

TECHNICAL FIELD

The present invention relates to anti-microbial compositions and more particularly to anti-microbial compositions that have a very high initial microbial kill rate and then remain active for an extended period of time. The anti-microbial compositions can also reduce and/or prevent odors.

BACKGROUND

With the increasing awareness of the simple pathways that infectious bacteria can take into our bodies and the detrimental consequences that can occur, new technologies have been developed to decrease the probability of infection. Many areas outside the hospital, such as sporting and fitness facilities have seen an increase in bacterial infections via organisms such as Methicillan-resistant *Staphylococcus aureus* (MRSA). *Staphylococcus aureus* is commonly found on human skin and thus, can be transferred onto a surface and into the body. Anti-microbial compositions that remain active throughout a coating's lifetime may be useful in preventing non-healthcare related bacterial infections. Additionally, such compositions may also be useful in reducing and/or preventing odors associated with bacterial build-up on a surface.

SUMMARY

One embodiment of the invention is an anti-microbial composition including an anti-microbial polymer containing silicon-containing quaternary ammonium groups, polyvinyl alcohol (PVA), at least one short chain alcohol, optional fragrance, and water.

Another embodiment is an anti-microbial composition including 0.1-10 wt % of an anti-microbial polymer containing silicon-containing quaternary ammonium groups, 0.1-10 wt % polyvinyl alcohol (PVA), 1.0-20 wt % isopropyl alcohol, optional fragrance, and water.

A further embodiment is a method for disinfecting a surface by applying the anti-microbial composition disclosed herein. The composition may be applied to porous or non-porous surfaces.

While multiple embodiments are disclosed, still other embodiments of the present invention will become apparent to those skilled in the art from the following detailed description, which shows and describes illustrative embodiments of the invention. Accordingly, the detailed description is to be regarded as illustrative in nature and not restrictive.

DETAILED DESCRIPTION

According to various embodiments, the present invention is an active, anti-microbial composition for treating a surface. A wide variety of porous and non-porous surfaces can be treated using the anti-microbial composition according to the embodiments of the present invention. Exemplary surfaces to be treated using the anti-microbial composition of the present invention include, but are not limited to, the following: exercise equipment and machines; sports equipment such as, for example, helmets, pads and other protective gear; and exercise mats such as, for example, yoga mats, wrestling mats, martial arts mats and gymnastic mats. Polyamide surfaces may be particularly suitable for treatment.

The composition is non-toxic and includes a non-leaching anti-microbial component that remains active throughout the coating's lifetime. In one embodiment, the anti-microbial composition remains effective against bacteria for a period of up to 60 days. In another embodiment, the anti-microbial composition remains effective against bacteria for a period of up to 90 days. In still yet other embodiments, the anti-microbial composition remains effective against bacteria after a period of 90 days. The anti-microbial composition is also effective in reducing and/or preventing odors.

According to one embodiment, the anti-microbial composition comprises, consists or consists essentially of at least one anti-microbial polymer containing silicon-containing quaternary ammonium groups, polyvinyl alcohol (PVA), at least one short chain alcohol, optional fragrance(s), and water.

The anti-microbial polymer containing silicon-containing quaternary ammonium groups may have the following formula:

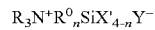

$$R_3N^+R^0{}_nSiX'_{4-n}Y^-$$

wherein each R and each $R^0$ is independently a non-hydrolysable organic group, such as, without limitation, an alkyl group of 1 to about 22 carbon atoms or an aryl group, for example, phenyl; n is an integer of 0 to 3; each X' is —OR', wherein R' is an alkyl group of 1 to about 22 carbon atoms, or an aryl group of 6 carbon atoms. More particularly, each of the R groups is independently methyl, ethyl, propyl, butyl, octyl, dodecyl, tetradecyl or octadecyl; each of the $R^0$ groups is independently methylenyl, ethylenyl, propylenyl, butylenyl, octylenyl, dodecylenyl, tetradecylenyl or octadecylenyl; and each X' is —OR', wherein R' is methyl, ethyl, propyl or butyl; and even more preferably, methyl or ethyl. Y is a suitable anionic moiety to form the salt of the polymer, such as halide, hydroxyl, acetate, $SO_4^{-2}$, $CO_3^{-2}$ and a $PO_4^{-2}$ counter ion. More particularly, Y is a halide.

Exemplary polymers of this type are shown and described in U.S. Pat. No. 6,572,926 entitled "Biostatic Product Using Interpenetrating Network Polymers," U.S Published Application No. 2006/0217515 entitled "Method of Creating a Sustained Silicon-Containing Quaternary Ammonium Antimicrobial Agent Within a Polymeric Material," and U.S. Published Application No. 2006/0223962 entitled "Method of Creating a Solvent-Free Polymeric Silicon-Containing Quaternary Ammonium Antimicrobial Agent Having Superior Sustained Antimicrobial Properties," all of which are incorporated herein by reference in their entireties for all purposes.

A particularly suitable silicon-containing quaternary ammonium polymer is polymeric 3-(trimethoxysilyl) propyldimethyloctadecyl ammonium chloride, which is commercially available from BIOSAFE® of Pittsburgh, Pa. In one embodiment the anti-microbial composition includes, about 0.1 wt % to about 10 wt %, more particularly about 0.5 wt % to about 5 wt %, even more particularly about 0.75 wt % to about 2.5 wt % silicon-containing quaternary ammonium polymer. In another embodiment, the anti-microbial composition includes about 1 wt % silicon-containing quaternary ammonium polymer.

The anti-microbial composition also includes PVA, which may cause the composition to form a thin protective film over a treated surface and/or improve the stability of the composition prior to application. In one embodiment the anti-microbial composition includes from about 0.1 wt % to about 10 wt. %, more particularly about 0.5 wt % to about 5 wt %, even more particularly about 0.75 wt % to about 2.5 wt % PVA. In another embodiment, the anti-microbial composition includes about 1 wt % PVA.

The anti-microbial composition further includes at least one short chain and/or monohydric alcohol such as ethanol, propanol or isopropyl alcohol. In one embodiment, the anti-microbial composition includes about 1 wt % to about 20, wt %, more particularly about 5 wt % to about 15 wt %, even more particularly about 8 wt % to about 12 wt % of the alcohol. In another embodiment, the anti-microbial composition includes about 10 wt. % of the alcohol.

Optionally, anti-microbial composition may include one or more fragrances. Suitable fragrances are soluble in either water or alcohol. A fragrance may be chosen in part based on its vapor pressure, which impacts the period of time during which the fragrance can be detected. In one embodiment the fragrance has a vapor pressure of about 0.005 mm Hg to about 0.2 mm Hg at 20° C., more particularly, 0.01 to about 0.1 mm Hg at 20° C. In another embodiment, the anti-microbial composition includes at least two fragrances with different vapor pressures. For example, the anti-microbial composition may include a first fragrance having a vapor pressure of from 0.005 mm Hg to about 0.05 mm Hg at 20° C., more particularly 0.005 mm Hg to about 0.02 mm Hg at 20° C., and a second vapor pressure of from 0.05 mm Hg to about 0.2 mm Hg at 20° C., more particularly, about 0.05 mm Hg to about 0.1 mm Hg at 20° C. In these embodiments, the fragrance with the higher vapor pressure is detectable upon application, but disperses relatively quickly. The fragrance with the lower vapor pressure remains detectable over a more extended period of time. The anti-microbial composition may include from about 0.05 wt % to about 0.5 wt %, more particularly from about 0.1 wt % to about 0.3 wt %, and even more particularly about 0.2 wt. % fragrance.

The anti-microbial composition may be produced and/or used in a liquid (e.g., non-gel) form with an aqueous carrier. In one embodiment, a use solution of the anti-microbial composition may include about 59.5 wt % to about 98.75 wt %, more particularly, about 75 wt % to about 95 wt %, even more particularly, about 80 wt % to about 90 wt % water. In another embodiment, the anti-microbial composition includes 87.8-88 wt. % water. In another embodiment, the anti-microbial composition may have a viscosity, as measured at 25° C. with a DV-II+ Brookfield viscometer with a UL Adaptor, of less than 4.0 cP, more particularly, less than 3.5 cP. In a further embodiment, the anti-microbial composition is free of one or more of buffers, pH modifiers, anionic surfactants, and/or additional disinfecting agents such as sodium hypochlorite. Exemplary anti-microbial compositions may have the following formulations:

| Material | Embodiment 1 (wt %) | Embodiment 2 (wt %) | Embodiment 3 (wt %) | Embodiment 4 (wt %) |
|---|---|---|---|---|
| SI quaternary ammonium polymer | 0.1-10 | 0.5-5.0 | 0.75-2.5 | 1.0 |
| PVA | 0.1-10 | 0.5-5.0 | 0.75-2.5 | 1.0 |
| IPA | 1-20 | 5-15 | 8-12 | 10 |
| Fragrance | 0.05-0.5 | 0.1-0.3 | 0.1-0.3 | 0.2 |
| Water | Balance | Balance | Balance | 87.8 |

In one exemplary embodiment, the anti-microbial composition can be applied to a surface to be treated by spraying the composition onto the surface with a mechanical or aerosol sprayer. In another embodiment, the anti-microbial composition can be applied to a surface using a fibrous or porous material saturated in the composition (e.g. a towelette) to wipe the surface. As further shown in the examples set forth below, the initial application of the anti-microbial composition may be effective in destroying bacteria present on the treated surface. Moreover, the treated surface remains resistant to bacterial growth for period of at least 90 days, more particularly, at least 60 days.

EXAMPLE 1

Materials and Application

An anti-microbial composition (Formula 1) was prepared, which contained 1 wt. % of an anti-microbial polymer containing silicon-containing quaternary ammonium groups (BIOSAFE® polymer), 1 wt. % polyvinyl alcohol (PVA), 10 wt. % isopropyl alcohol, 0-0.2 wt. % fragrance, and 87.8-88 wt. % water. Formula 1 was prepared by mixing the anti-microbial polymer in water with vigorous mechanical stirring at a temperature above 80° C. for at least four hours. The resulting solution was vacuum filtered through a 0.45 micron filter to obtain a clear solution, which was then reduced to room temperature. A PVA solution was prepared by mixing PVA in water, heating above 80° C. until a clear solution was obtained and then reducing the temperature. The antimicrobial polymer solution and the PVA solution were then combined. Fragrance was added to the isopropyl alcohol and the alcohol was slowly combining with the polymer solution containing the PVA and the anti-microbial polymer. Formula 1 was applied to vinyl surface of several mats in a mixed martial arts facility in a substantially uniform manner with a mop, and were then allowed to dry prior to being subjected to normal use. One mat was tested after 30 days and the other was tested after 90 days.

Media

Neutralizer was made by dispensing 50 mL of Letheen Broth (pH of 7±0.5) into wide mouth bottles followed by sterilization for 15-20 minutes in an autoclave at 121° C. Tryptic Soy Agar (TSA) was sterilized for 20 minutes in an autoclave at 121° C., and approximately 15 mL was dispensed into each sterile Petri dish. 100 mL of Tryptic Soy Broth (TSB) was placed into a capped 250 mL Erlenmeyer flask and sterilized for 20 minutes in an autoclave at 121° C. 25 mL aliquots of saline solution (0.85% NaCl) were added to a series of test tubes and sterilized for 15-20 minutes at 121° C. 10 mL of the slurry inoculum carrier (8.5 g NaCl, 3.0 g Agar, 1000 mL deionized water) was placed into each test tube and sterilized for 15-20 minutes at 121° C.

Test Article Preparation

The treated mats and an untreated vinyl control were pre-cleaned with detergent to remove any excess dirt and dust from the surface. They were then air-dried, cut into 5.5±0.1 cm diameter circles and placed, treated side down, into sterile Petri dishes. The backside of the fabric was then exposed to Ultra Violet (UV) light in a biological cabinet for approximately four hours. This step was performed in order to reduce contaminants on the backside of the sample, as the entire sample was placed in neutralizer.

Inoculum Preparation

The test organism, *Staphylococcus aureus*, American Type Culture Collection No. 6538, a gram positive organism, was grown in 100 mL TSB at 37±2° C. for 24-48 hours. The Optical Density (OD) of the culture was measured at 550 nm to estimate the cell concentration. An OD of 0.2 contains about 5×10$^7$ colony forming units per milliliter (cfu/mL). The appropriate dilutions were made, and the final dilution was placed into the slurry inoculum carrier. The final concentration in the inoculum was approximately 10$^4$ cfu/mL.

100 µL of the slurry inoculum mixture was placed onto the samples and spread over the surface using sterile spreaders. After the contact times of 60 and 90 minutes, the samples were aseptically placed into wide mouth bottles containing 50 mL of neutralizer. The bottles were then shaken and sonicated for 5 minutes. The bottles were shaken for one additional minute, and the entire contents of the bottle (dilutions were made for control samples) were filtered through 0.2 µm membrane filters and placed onto TSA plates. All of the plates were then incubated for 48 hours at 37±2° C.

Table 1 below shows the test results for each of the samples. The results illustrate that the 30 and 90 day surface treated mats achieved almost identical results at 60 and 90 minutes after innoculation. Both mats achieved over a 99% reduction of Staphylococcus aureus at both time points.

TABLE 1

Results of Surface Treated Mat Testing

CFU Recovered After Contact Time

| Sample Description | 60 minutes | % Reduction | 90 Minutes | % Reduction |
|---|---|---|---|---|
| 30 Day Use Mat Sample 1 | 2 | 99.8 | 2 | 99.8 |
| 30 Day Use Mat Sample 2 | 3 | 99.8 | 1 | 99.9 |
| 30 Day Use Mat Sample 3 | 0 | 100.0 | 2 | 99.8 |
| 90 Day Use Mat Sample 1 | 2 | 99.8 | 1 | 99.9 |
| 90 Day Use Mat Sample 2 | 0 | 100.0 | 9 | 99.2 |
| 90 Day Use Mat Sample 3 | 26 | 97.9 | 9 | 99.2 |
| Non-Treated Mat Control | 1230 | — | 1160 | — |

The data demonstrates that the anti-microbial efficacy of the anti-microbial composition remained for at least 90 days after application even after regular use at a mixed martial arts facility. The test organism, Staphylococcus aureus, demonstrates a very similar resistance to germicides as Methicillan-resistant Staphylococcus aureus (MRSA) does, given that it varies only in the genetics that lead to antibiotic resistance.

EXAMPLE 2

Formula 1 utilized in Example 1 and a second composition (Formula 2) that did not contain isopropyl alcohol were prepared and evaluated for their effectiveness in reducing existing Staphylococcus aureus and Pseudomonas aeruginosa populations. The composition of each sample is provided in Table 2 below.

TABLE 2

|  | Formula 2 | Formula 1 |
|---|---|---|
| Polyvinyl alcohol (PVA) | 1% | 1% |
| BIOSAFE ® polymer | 1% | 1% |
| Isopropyl alcohol | — | 10% |
| Fragrance | — | 0.2% |
| Water | 98% | 87.8% |

Neutralizer/Inoculum Preparation:

Neutralizer was made by dispensing 50 mL of Letheen Broth (pH of 7 0.5) into Benji jars followed by sterilization for 15-20 minutes in an autoclave at 121° C. Tryptic Soy Agar (TSA) was sterilized for 20 minutes in an autoclave at 121° C., and approximately 15 mL was dispensed into each sterile Petri dish. 100 mL of Tryptic Soy Broth (TSB) was placed into a capped 250 mL Erlenmeyer flask and sterilized for 20 minutes in an autoclave at 121° C. for the Pseudomonas aeruginosa and Staphylococcus aureus. To run the experiments, 9 ml of sample formula was placed in a 20° C. water bath for ten minutes. Then, 1 mL of bacteria was added and the timer was started. At each time point the samples were vortexed and 1 mL was added to 50 mL of Letheen Broth neutralizer. The remaining solution was placed back into the water bath until the following time point. Each sample was filtered and placed on TSA plates incubated for 24-48 hours and read.

The effectiveness of each sample against each type of bacteria was evaluated by determining the log reduction of the bacterial populations at two minutes, five minutes, and ten minutes. The data is presented below in Table 3.

TABLE 3

| Formula | Time (min) | Staph. (cfu) | log reduction | Pseud. (cfu) | log reduction |
|---|---|---|---|---|---|
| 2 | 2 | TNTC | — | TNTC | — |
|  | 2 | TNTC | — | TNTC | — |
| 1 | 2 | 0 | 8 | 0 | 8 |
|  | 2 | 1 | 8 | 0 | 8 |
| 2 | 5 | TNTC | — | TNTC | — |
|  | 5 | TNTC | — | TNTC | — |
| 1 | 5 | 0 | 8 | 0 | 8 |
|  | 5 | 0 | 8 | 0 | 8 |
| 2 | 10 | TNTC | — | TNTC | — |
|  | 10 | TNTC | — | TNCTC | — |
| 1 | 10 | 0 | 8 | 0 | 8 |
|  | 10 | 0 | 8 | 0 | 8 |
| NV1 | — | TNTC | — | TNTC | — |
| NV2 | — | TNTC | — | TNTC | — |

TNTC = Too numerous to count
NV = neutralizer validation

The results show that upon initial application to a surface and prior to its drying, Formula 1, which includes alcohol, is very efficacious against the two types of bacteria populations in a short period time. The solution can reduce Staph. and Pseud. populations by 99.999999% in two minutes. Without the inclusion of alcohol (Solution 1), Solution 1 did not achieve any measureable reduction in two, five or ten minutes. The neutralizer validations show that the neutralizers used were not toxic to the bacteria tested, and that they were effective in stopping the antibacterial activity at the indicated contact times, thus validating the tests.

EXAMPLE 3

An aqueous solution containing 1.0 wt % BIOSAFE® polymer was divided into two equal portions. An additional 1.0 wt % PVA was added to one of the portions while no additional components were added to the other portion. Each portion was separated into three samples, placed in sealed containers and frozen at about −15° C. The containers were brought back to room temp without applying additional heat. Each sample that included the PVA melted back into a homogenous solution, while the samples that did not include PVA had a large volume of white precipitate separate out of solution. This experiment indicates that the addition of PVA to the antimicrobial compositions of the present invention improves compositional stability under certain environmental conditions.

EXAMPLE 4

The same experiment described in Example 3 was performed, but the containers were gently heated (−50-60° C.) to bring the solutions back to liquid form. The samples with PVA added, once again, became homogeneous liquid solutions. The solutions without PVA became homogeneous solutions as well, but the viscosity drastically increased. This experiment indicates that the addition of PVA to the antimicrobial compositions of the present invention improves compositional stability under certain environmental conditions.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A liquid film forming anti-microbial composition consisting of:
   1 wt. % of an anti-microbial polymer containing silicon-containing quaternary ammonium groups by weight of the composition;
   1 wt. % polyvinyl alcohol (PVA) by weight of the composition;
   10 wt. % ethanol by weight of the composition;
   0-0.2 wt. % fragrance by weight of the composition; and
   87.8-88 wt. % water by weight of the composition.

2. The liquid film forming antimicrobial composition of claim 1 wherein the anti-microbial polymer containing silicon-containing quaternary ammonium groups has the formula:

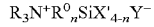

wherein each R and each R⁰ is independently a non-hydrolysable organic group selected from an alkyl group of 1 to about 22 carbon atoms and an aryl group; n is an integer of 0 to 3; each X' is —OR', wherein R' is selected from an alkyl group of 1 to about 22 carbon atoms, and an aryl group of 6 carbon atoms.

3. The liquid film forming antimicrobial composition of claim 2 wherein each R group is independently selected from methyl, ethyl, propyl, butyl, octyl, dodecyl, tetradecyl and octadecyl; each R⁰ group is independently selected from methylenyl, ethylenyl, propylenyl, butylenyl, octylenyl, dodecylenyl, tetradecylenyl and octadecylenyl; and each X' is —OR', wherein R' is selected from methyl, ethyl, propyl and butyl.

4. The liquid film forming antimicrobial composition of claim 1 wherein the anti-microbial polymer containing silicon-containing quaternary ammonium groups is polymeric 3-(trimethoxysilyl) propyldimethyloctadecyl ammonium chloride.

5. The liquid film forming antimicrobial composition of claim 1 wherein the composition has a viscosity of less than 4 cP.

6. A method of disinfecting a surface comprising applying a liquid film forming anti-microbial composition to the surface, the liquid film forming anti-microbial composition consisting of 1% by weight of an anti-microbial polymer containing silicon-containing quaternary ammonium groups, 1% by weight of polyvinyl alcohol (PVA), 10 wt. % ethanol, 0-0.2 wt. % fragrance, and 87.8-88% by weight water.

7. The method of claim 6 wherein the surface comprises a porous surface.

8. The method of claim 6 wherein the surface comprises a non-porous surface.

9. The method of claim 6 wherein the surface comprises a polyamide material.

* * * * *